United States Patent
Rasche et al.

(10) Patent No.: US 6,869,217 B2
(45) Date of Patent: Mar. 22, 2005

(54) X-RAY DEVICE PROVIDED WITH A ROBOT ARM

(75) Inventors: Volker Rasche, Hamburg (DE); Hermann Schomberg, Hamburg (DE); Erhard Paul Artur Klotz, Neumuenster (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/732,200

(22) Filed: Dec. 7, 2000

(65) Prior Publication Data

US 2001/0005410 A1 Jun. 28, 2001

(30) Foreign Application Priority Data

Dec. 7, 1999 (DE) .................................. 199 58 864

(51) Int. Cl.⁷ .................................................. H05G 1/02
(52) U.S. Cl. ...................................... 378/197; 378/193
(58) Field of Search .............................. 378/197, 198, 378/193, 196

(56) References Cited

U.S. PATENT DOCUMENTS

| | | | | | |
|---|---|---|---|---|---|
| 3,281,598 A | * | 10/1966 | Hollstein | ..................... | 378/179 |
| 3,644,735 A | * | 2/1972 | Vandervelden | .............. | 378/205 |
| 3,784,837 A | * | 1/1974 | Holmström | ................. | 378/189 |
| 4,358,856 A | * | 11/1982 | Stivender et al. | ........... | 378/167 |
| 4,775,994 A | * | 10/1988 | Kranvogel | ................. | 378/197 |
| 4,894,855 A | * | 1/1990 | Kresse | ....................... | 378/189 |
| 4,987,583 A | * | 1/1991 | Travanty et al. | ............. | 378/91 |
| 5,103,472 A | * | 4/1992 | Takagi | ......................... | 378/197 |
| 5,285,772 A | * | 2/1994 | Rattner | .......................... | 601/4 |
| 5,410,584 A | * | 4/1995 | Schaefer et al. | ............ | 378/196 |
| 5,428,660 A | * | 6/1995 | Daniel, Jr. | ................... | 378/197 |
| 5,485,502 A | * | 1/1996 | Hinton et al. | ................ | 378/117 |
| 5,521,957 A | * | 5/1996 | Hansen | ........................ | 378/198 |
| 5,654,997 A | | 8/1997 | Brownell et al. | ........... | 378/117 |
| 5,901,200 A | * | 5/1999 | Krause | ........................ | 378/198 |
| 6,213,638 B1 | * | 4/2001 | Rattner | ....................... | 378/198 |

FOREIGN PATENT DOCUMENTS

| | | | | |
|---|---|---|---|---|
| DE | 3604955 A1 | 8/1987 | ............ | A61B/6/10 |
| DE | 19625407 A | 1/1998 | ............ | A61B/6/02 |
| FR | 2645007 | * 10/1990 | ............ | A61B/6/03 |
| FR | 2645007 A1 | 10/1990 | ............ | A61B/6/03 |
| JP | 06-105831 | * 4/1994 | ............ | A61B/6/00 |
| JP | 11-258492 | * 10/1999 | ............ | A61B/6/04 |
| JP | 11-285492 | * 10/1999 | ............ | A61B/6/04 |
| WO | WO9930614 | 6/1999 | ............ | A61B/6/00 |

* cited by examiner

Primary Examiner—Edward J. Glick
Assistant Examiner—Chih-Cheng Glen Kao

(57) ABSTRACT

The invention relates to an X-ray device which includes an X-ray source and an X-ray detector which are mounted at a respective end of a common holding device. The holding device being attached to the room by way of a supporting device. In order to realize a more flexible construction of such X-ray devices that are widely used and are usually provided with a holding device in the form of a C-arm and nevertheless maintain a high positioning accuracy. The invention further relates to a supporting device constructed with a plurality of hinged, serially interconnected supporting members. The supporting device is formed notably by a serial manipulator, for example, a conventional robot arm.

22 Claims, 4 Drawing Sheets

X-RAY DEVICE PROVIDED WITH A ROBOT ARM

BACKGROUND OF THE INVENTION

1. Field of the Invention

The invention relates to an x-ray device provided with an X-ray source and an X-ray detector which are mounted at a respective end of a common holding device, the holding device being connected to the room by way of a supporting device, wherein the supporting device is composed of a plurality of hinged, serially interconnected supporting members.

2. Description of the Related Art

Furthermore, WO 99/30614 discloses a C-arm X-ray device in which the supporting device is constructed as a parallel manipulator. Therein, a first holding plate that is attached to the C-arm is connected to a second holding plate via a plurality of supporting members; the second holding plate can be attached, for example, to the wall. Each of said supporting members; is connected directly to both holding plates, the points of connection of the supporting members to the holding plates being different. The C-arm can thus be moved to given positions within given limits.

U.S. Pat. No. 4,894,855 discloses an X-ray device in which the X-ray tube, the X-ray detector and the patient table are mounted on a respective manipulator which consists of a plurality of supporting members, thus enabling a motion of these elements in all three spatial directions that is independent of one another.

It has been found that the solution known from WO 99/30614 has the drawback that the flexibility and the possibilities for movement are limited notably because of the mechanical construction. For many applications, for example for 3D rotation angiography, however, it is necessary to form X-ray images from a large variety of positions, that is, that for example a series of X-ray projection images can be formed along a predetermined trajectory. This should also take place with an as high as possible positioning accuracy. Granted, the X-ray device known from U.S. Pat. No. 4,894,855 offers a high flexibility, but the accuracy that can be achieved thereby is not adequate for many applications. Moreover, it requires a plurality of manipulators, each of which must be separately controlled; this leads to high costs and necessitates complex control.

Therefore, it is an object of the invention to provide an as flexible as possible X-ray device which offers a high positioning accuracy and can be manufactured as economically as possible.

This object is achieved by means of an X-ray device as disclosed in claim 1.

The invention is based on the recognition of the fact that neither a rigid supporting device nor a supporting device in the form of a parallel manipulator constitutes the optimum solution with respect to flexibility. Therefore, the supporting device according to the invention is composed of a plurality of hinged, serially interconnected supporting members which are preferably also individually controllable so that the holding device can be moved in all spatial directions. The necessary positioning accuracy is also achieved in that the holding device is preferably constructed so as to be rigid, so that the distance between the X-ray tube and the X-ray detector and the orientation of these elements relative to one another are invariable. Moreover, in this case only the supporting device is composed of a plurality of supporting members that must be controlled, whereas the X-ray device that is known from U.S. Pat. No. 4,894,855 includes a plurality of manipulators that must be separately controlled.

The supporting device in a preferred embodiment of the invention is a serial manipulator, notably a robot arm. Use can be made notably of a serial robot arm as is known from many manufacturing technical fields. This may lead to a reduction of costs, because the numbers in which C-arm X-ray devices are manufactured are very small, so that the cost of manufacturing the mechanical systems constitutes a significant cost factor. The use of a conventional robot arm that is manufactured in large numbers, however, enables the cost of this part of the mechanical system to be reduced to some extent while the freedom of movement is increased at the same time. Such robot arms can be simply controlled by means of known and standardized software. Because robot arms of this kind also operate at a high speed, the period of time required for the formation of X-ray images could also be reduced. For example, a real-time study of the blood flow could be possible.

The supporting device in a preferred further embodiment is constructed in such a manner that the X-ray source and the X-ray detector can be positioned completely as desired and/or the motions of the individual supporting members of the supporting device are controllable. In order to enable the X-ray tube to follow circular or helical trajectories as required in rotation angiography, the supporting device in a further preferred embodiment yet is connected to the holding device by way of a hinge.

Even though the holding device is preferably constructed as a rigid C-arm, the holding device may alternatively be composed of at least two holding members, the X-ray source being mounted on a first holding member whereas the X-ray detector is mounted on the second holding member. This offers the advantage that the distance between the X-ray source and the X-ray detector can also be changed, so that the imaging scale and the size of the examination zone can be varied and the overall flexibility is further enhanced.

Conventional robot systems usually have a mechanical emergency braking system for stopping the motion of the robot in the case of a failure or incorrect control. Because injury of a patient must be avoided at all costs in medical applications, a preferred embodiment is provided with means for monitoring the distance between an object to be examined and moving parts of the X-ray device, notably the X-ray source and the X-ray detector; for example, ultrasound sensors and ultrasound detectors can be used for this purpose. They continuously measure the distance between the moving parts and the object to be examined and initiate emergency braking as soon as the distance becomes too small and a risk of injury of the object to be examined arises. The distance initiating such an emergency braking operation, however, should be adjusted in such a manner that on the one hand all necessary X-ray images can still be formed while on the other hand emergency braking is still possible within the distance remaining before contact occurs.

Further feasible means for monitoring the distance consist of mechanical contact sensors mounted on the X-ray source and the X-ray detector, for example feeler-like sensors in the form of long bristles which produce a sensor signal upon contact with the object to be examined, so that emergency braking can be initiated. Another feasible means for monitoring is a separate video system which continuously monitors the motion of the X-ray source and the X-ray detector in real time so as to evaluate this motion and initiate emergency braking when the distance becomes too small.

BRIEF DESCRIPTION OF THE DRAWING FIGURES

The invention will be described in detail hereinafter with reference to the drawings. Therein:

DETAILED DESCRIPTION OF THE INVENTION

Figure 1:
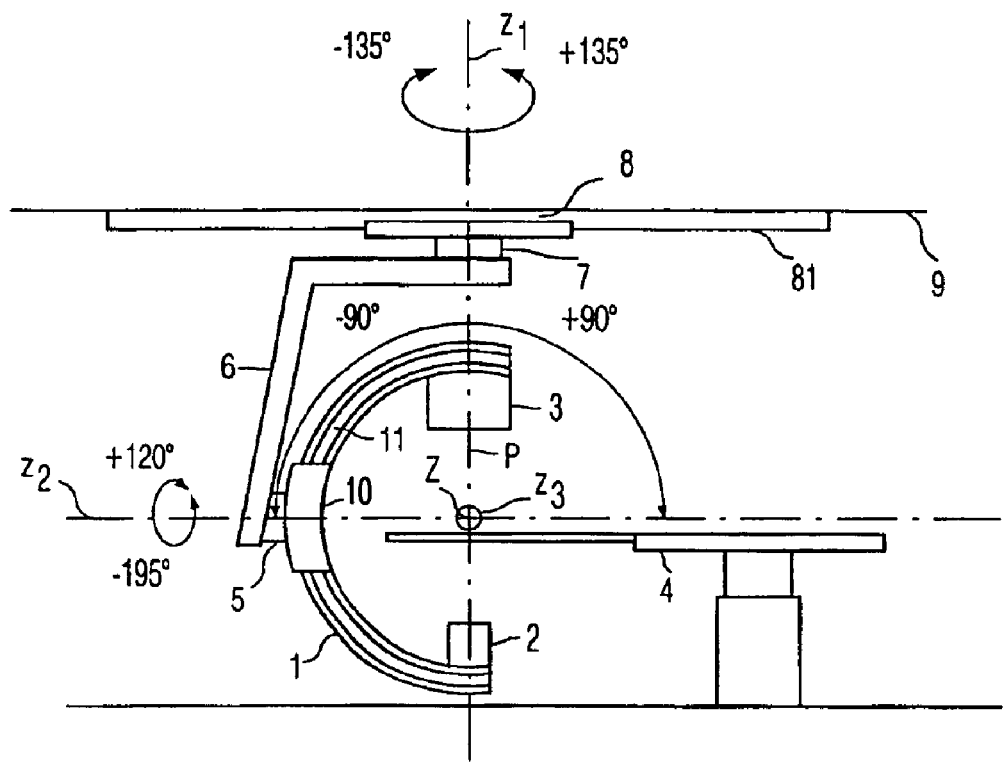
FIG. 1 shows a known C-arm X-ray device.

The known X-ray device that is shown in FIG. 1 has a holding device in the form of a C-arm 1 with an X-ray tube 2 and an X-ray detector 3. The tube and the detector are oriented relative to one another in such a manner that X-rays emanating from the X-ray tube 2 along the projection radius P traverse an object to be examined that is arranged on the patient table 4 in the examination zone Z and are incident on the X-ray detector 3. The X-ray tube 2 and the X-ray detector 3 are rotatable about the $z_3$ axis in the given angular range via rails 11 which are provided on the C-arm 1 and extend through a rail holding system 10. The rail holding system 10 is connected to a rigid supporting device 6 via a hinge 5 that allows a rotation of 315° about the $z_2$ axis in the case shown. The latter device itself is mounted, via a hinge 7 which enables rotation about the $z_1$ axis, on a slide 8 which is displaceable in a system of rails 81 which itself is attached to the ceiling 9. As is already indicated by the angles given, the degree of freedom is limited in such an X-ray device.

Figure 2:
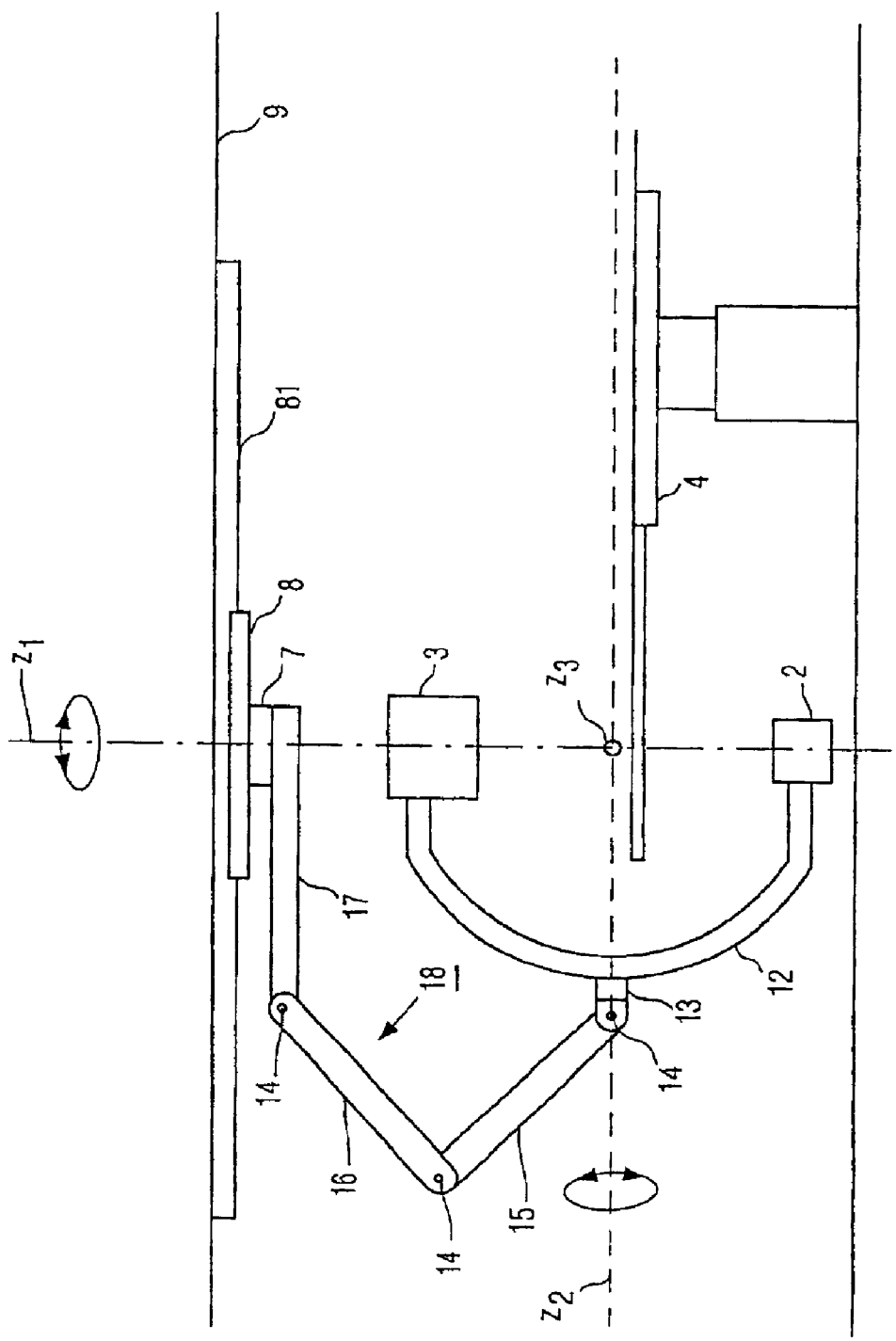
FIG. 2 shows a C-arm X-ray device in accordance with the invention.

FIG. 2 shows a first embodiment of an X-ray device in accordance with the invention. First of all, the holding device 12 therein is constructed as a significantly simpler rigid C-arm without rails. The holding device 12 is connected to the supporting device 18 via a hinge 13 that enables rotation through 360° about the $Z_2$ axis. In the case illustrated the supporting device 18 includes three supporting arms 15, 16, 17 which are serially connected to one another via simple, plane hinges 14 and to the hinge 7 at one end and to the hinge 13 at the other end. The hinges 14 enable the position of the holding device 12 to be changed in the plane defined by the supporting arms 15 and 16. The attachment to the ceiling 9 is the same as for the X-ray device shown in FIG. 1. As can be readily seen, the construction of the supporting device 18 enables significantly more flexible positioning of the holding device 12. Granted, the construction of the supporting device 18 is larger in comparison with the construction of the supporting device 6 (see FIG. 1), but compensation is provided by the fact that in this case the supporting device 12 may be constructed so as to be considerably simpler, notably without rails, and also significantly lighter.

In order to enhance the flexibility of such an X-ray device even further, moreover, the X-ray tube 2 and/or the X-ray detector 3 can be mounted on the C-arm 12 by way of a displacement device in such a manner that they can be displaced in the $z_1$ direction.

Figure 3:
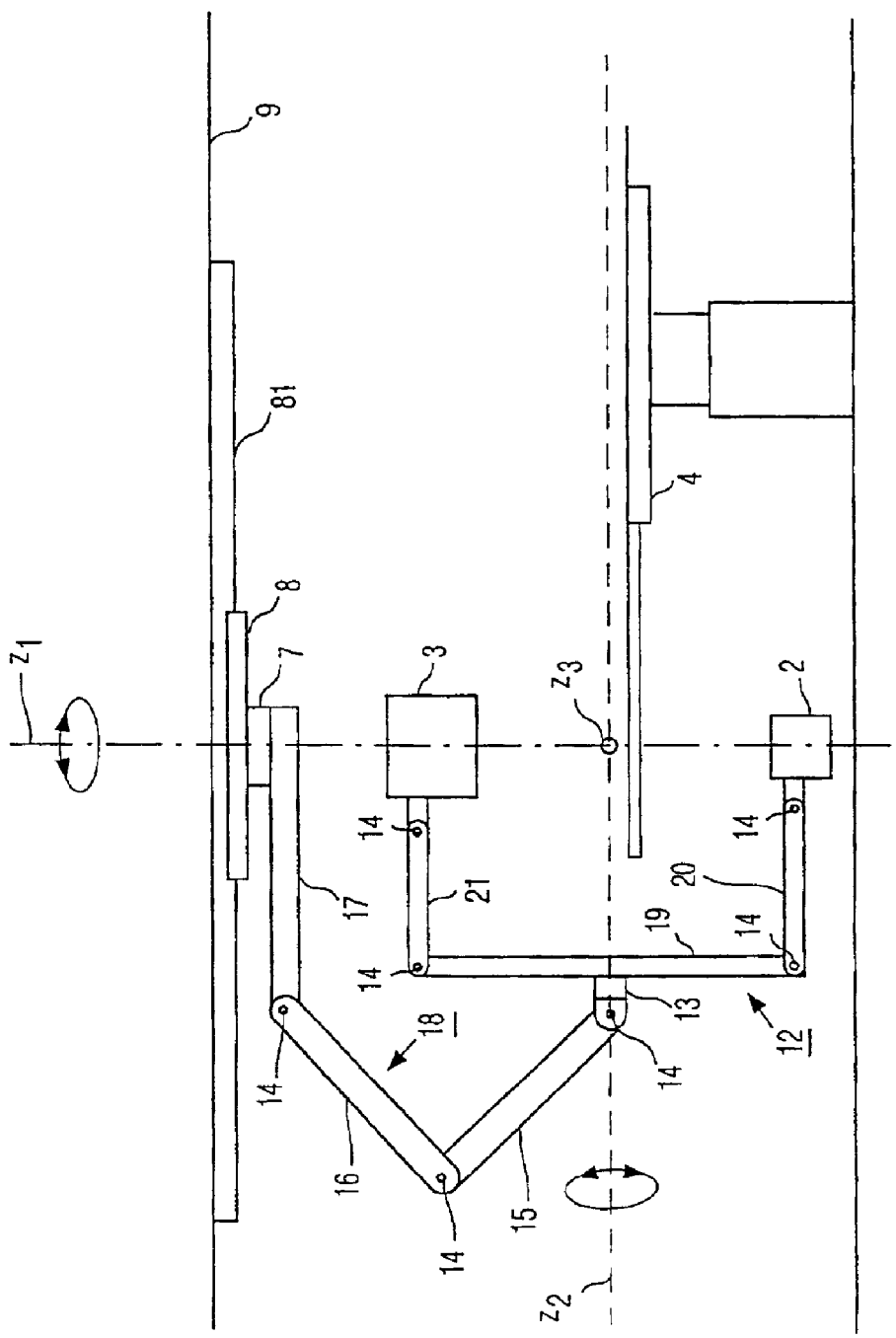
FIG. 3 shows a further embodiment of an X-ray device in accordance with the invention.

FIG. 3 shows a further embodiment of an X-ray device according to the invention. The supporting device 12 in this embodiment is constructed as for the X-ray device shown in FIG. 2; however, additionally the holding device 12 also consists of a number of holding members 19, 20, 21. These holding members form a somewhat polygonal "C" and are connected, via plane hinges 14, to one another and to the X-ray tube 2 or the X-ray detector 3. The distance between the X-ray tube 2 and the X-ray detector 3 can thus be varied and hence also the imaging scale.

Figure 4A:
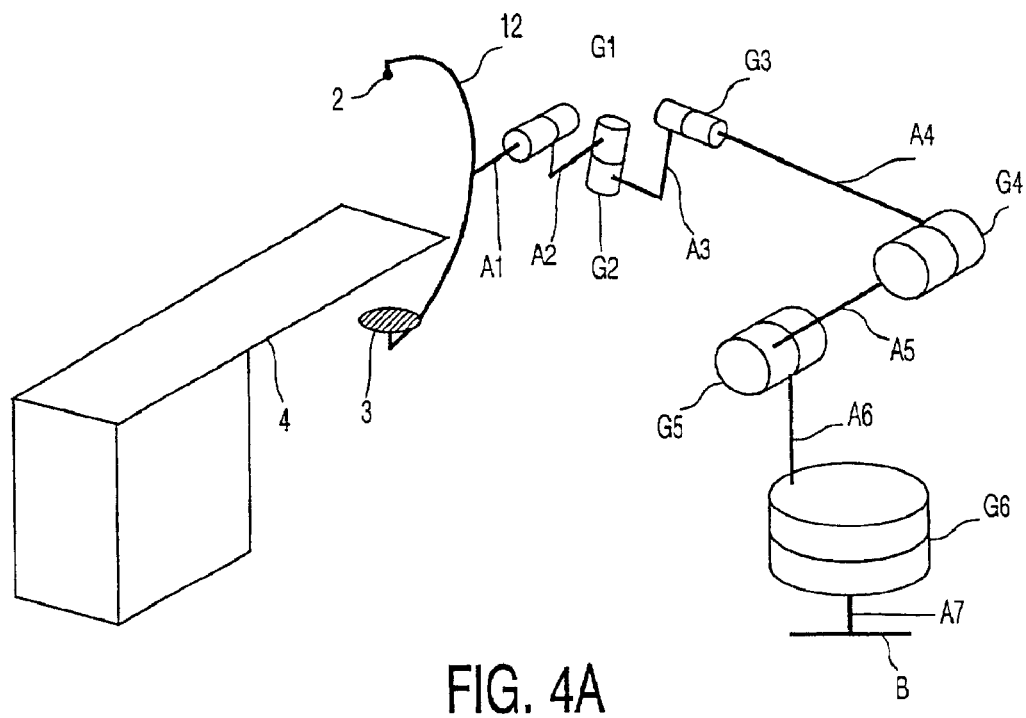
FIGS. 4a, 4b show diagrammatically a further embodiment of an X-ray device in accordance with the invention in different positions.
Figure 4B:
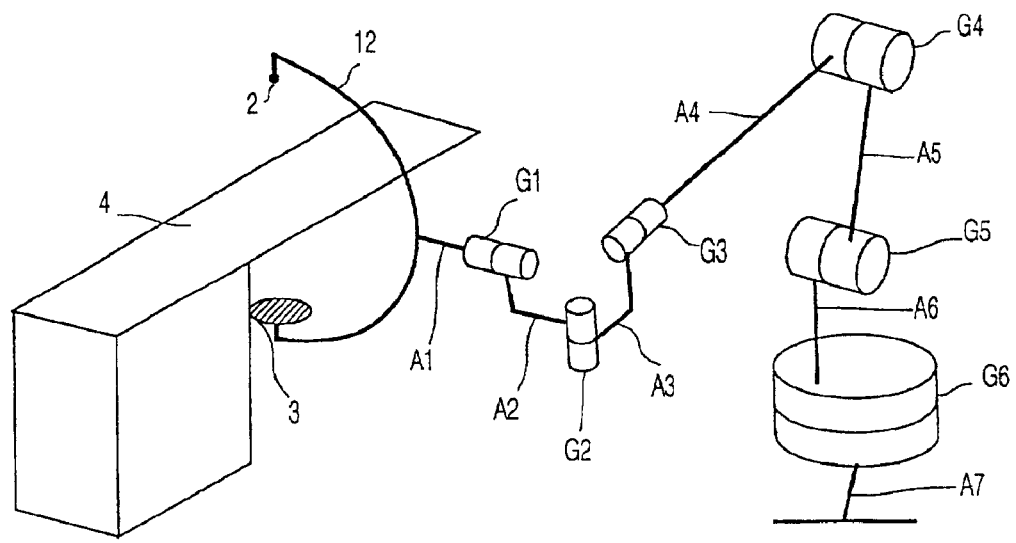

FIGS. 4a and 4b are diagrammatic representations of a further embodiment of an X-ray device in accordance with the invention in different positions. The connection from the holding device 12, which may be constructed as a simple C-arm as shown in FIG. 2, down to the floor B is realized by way of seven connection pieces $A_1$ to $A_7$ that are connected to one another via a respective hinge $G_1$ to $G_6$. Each of said hinges $G_1$ to $G_6$ enables rotation about an axis of rotation, so that the supporting device in this embodiment has six axes and offers the highest possible flexibility.

In FIG. 4a the C-arm 12 is arranged at the end of the patient table 4, for example in order to form a slice image of the head of a patient by means of rotation angiography. In FIG. 4b the C-arm 12 is arranged at the center of the patient table 4, for example in order to form an X-ray image of the abdomen of a patient. Such an X-ray device can be realized, for example by way of a conventional 6-axes flexible arm robot as frequently used in manufacturing techniques, for example for the manufacture of cars.

What is claimed is:

1. An X-ray device comprising:

an X-ray source and an X-ray detector which are mounted at different ends of a common holding device, the common holding device being connectable to a room by a supporting device, such that said supporting device has a first end connected to the common holding device and a second end connectable to the room, wherein the supporting device comprises a plurality of hinged, serially interconnected supporting members connected by six hinges, each of the hinges enabling rotation about an axis of rotation so that the supporting device has six separate axes of rotation, and wherein the one of the six hinges connected to the second end is a rotational hinge such that the entire supporting device is rotatable about an axis.

2. An X-ray device as claimed in claim 1, wherein the supporting device is a robot arm.

3. The X-ray device of claim 2, wherein the robot arm is controlled by software.

4. An X-ray device as claimed in claim 1, wherein the supporting device is constructed and connected to the holding device in such a manner that the common holding device with the X-ray source and the X-ray detector can be positioned completely as desired.

5. An X-ray device as claimed in claim 1, wherein the supporting device is connected to the holding device by one of the six hinges that permits rotation 360 degrees about an axis.

6. An X-ray device as claimed in claim 1, wherein the holding device is composed of at least two holding members, the X-ray source being mounted on a first holding member whereas the X-ray detector is mounted on a second holding member.

7. An X-ray device as claimed in claim 1, wherein the holding device is a C-arm.

8. An X-ray device as claimed in claim 1, further comprising means for monitoring the distance between an object to be examined and moving parts of the X-ray device including the X-ray source and the X-ray detector.

9. An X-ray device as claimed in claim 8, wherein the means for monitoring the distance are provided with ultrasound sensors and ultrasound detectors.

10. An X-ray device as claimed in claim 8, wherein the means for monitoring the distance include mechanical contact sensors.

11. The X-ray device of claim 10, wherein the mechanical contact sensors produce a signal upon contact with the object to be examined.

12. The X-ray device of claim 8, wherein emergency braking is initiated when the distance between the moving parts and the object to be examined fall below a safety threshold.

13. The X-ray device of claim 8, wherein the means for monitoring the distance include a separate video system to continuously monitor the motion of the X-ray source and the X-ray detector.

14. The X-ray device of claim 1, wherein the common holding device is rigid, such that the distance between the X-ray source and the X-ray detector and the orientation of both elements relative to one another are invariable.

15. The X-ray device of claim 1, wherein the X-ray source and the X-ray detector are mounted on the common holding device by a displacement device such that the X-ray source and the X-ray detector are displaceable along an axis.

16. The X-ray device of claim 1, wherein the second end of the supporting device is connected to the room at a connection point such that the rotational hinge permits rotation about an axis that extends perpendicularly out from the connection point.

17. The X-ray device of claim 1, wherein three of the six hinges of the supporting device are plane hinges.

18. An X-ray device comprising:
  an X-ray source and an X-ray detector which are mounted at different ends of a common holding device, the common holding device being connectable to a room by a supporting device,
  wherein the supporting device comprises a plurality of hinged, serially interconnected supporting members connected by six hinges, each of the hinges enabling rotation about an axis of rotation so that the supporting device has six separate axes of rotation, wherein the holding device is composed of at least two holding members, the X-ray source being mounted on a first holding member whereas the X-ray detector is mounted on a second holding member, and wherein the distance between the X-ray source and the X-ray detector is changeable by moving the first and second holding members such that an imaging scale and a size of the examination zone of the X-ray device are variable.

19. The X-ray device of claim 18, further comprising a third holding member connected to the supporting device, wherein each of said first and second holding members is connected to said third holding member via a hinge, said first and second holding members being individually controllable to change the distance between the X-ray source and the X-ray detector such that the imaging scale and the size of the examination zone of the X-ray device are variable.

20. The X-ray device of claim 18, wherein three of the six hinges of the supporting device are plane hinges.

21. An X-ray device comprising:
  an X-ray source and an X-ray detector which are mounted at different ends of a common holding device, the common holding device being connectable to a room by a supporting device,
  wherein the supporting device comprises a plurality of hinged, serially interconnected supporting members, such that the supporting device is a serial manipulator, and wherein the supporting device is a flexible arm comprising six separate hinges, each of the hinges enabling rotation about an axis of rotation such that the supporting device has six separate axes of rotation.

22. The X-ray device of claim 21, wherein three of the six hinges of the supporting device are plane hinges.

* * * * *